United States Patent [19]
Schwager

[11] Patent Number: 5,916,177
[45] Date of Patent: Jun. 29, 1999

[54] PRESSURE MEASURING GUIDE WIRE

[75] Inventor: Michael Schwager, Winterthur, Switzerland

[73] Assignee: Schneider (Europe) A.G., Bulach, Switzerland

[21] Appl. No.: 08/580,477

[22] Filed: Dec. 29, 1995

[51] Int. Cl.⁶ .................................................. A61B 5/00
[52] U.S. Cl. ........................ 600/585; 600/561; 600/485
[58] Field of Search ................................... 600/585, 485, 600/486, 488, 480, 561, 468

[56] References Cited

U.S. PATENT DOCUMENTS

| | | | |
|---|---|---|---|
| Re. 33,166 | 2/1990 | Samson ..................................... | 606/194 |
| 4,003,369 | 1/1977 | Heilman ..................................... | 128/2 |
| 4,582,181 | 4/1986 | Samson ..................................... | 128/348.1 |
| 4,721,117 | 1/1988 | Mar et al. ................................. | 128/772 |
| 4,724,846 | 2/1988 | Evans, III ................................. | 128/772 |
| 4,779,628 | 10/1988 | Machek ..................................... | 128/772 |
| 4,854,330 | 8/1989 | Evans, III et al. ....................... | 128/772 |
| 4,895,168 | 1/1990 | Machek ..................................... | 128/772 |
| 4,922,924 | 5/1990 | Gambale et al. .......................... | 128/772 |
| 4,953,553 | 9/1990 | Tremulis .................................... | 128/637 |
| 4,964,409 | 10/1990 | Tremulis .................................... | 128/657 |
| 4,971,490 | 11/1990 | Hawkins ..................................... | 128/772 |
| 5,050,606 | 9/1991 | Tremulis .................................... | 128/637 |
| 5,063,935 | 11/1991 | Gambale ..................................... | 128/657 |
| 5,127,917 | 7/1992 | Niederhauser et al. ................... | 606/191 |
| 5,180,376 | 1/1993 | Fischell ..................................... | 604/282 |
| 5,217,026 | 6/1993 | Stoy et al. ................................. | 128/772 |
| 5,267,574 | 12/1993 | Viera et al. ................................ | 128/772 |
| 5,345,945 | 9/1994 | Hodgson et al. .......................... | 128/772 |
| 5,376,083 | 12/1994 | Mische ...................................... | 604/264 |
| 5,404,886 | 4/1995 | Vance ........................................ | 128/772 |
| 5,425,724 | 6/1995 | Akins ......................................... | 604/284 |
| 5,429,139 | 7/1995 | Sauter ........................................ | 128/772 |
| 5,437,288 | 8/1995 | Schwartz et al. ......................... | 600/585 |
| 5,458,585 | 10/1995 | Salmon et al. ............................ | 604/280 |
| 5,511,559 | 4/1996 | Vance ........................................ | 128/772 |
| 5,527,292 | 6/1996 | Adams et al. ............................. | 604/171 |
| 5,527,298 | 6/1996 | Vance et al. .............................. | 604/280 |
| 5,569,197 | 10/1996 | Helmus et al. ............................ | 604/96 |
| 5,573,520 | 11/1996 | Schwartz et al. ......................... | 604/282 |
| 5,605,163 | 2/1997 | Hani ........................................... | 128/772 |
| 5,617,875 | 4/1997 | Schwager .................................. | 128/772 |

FOREIGN PATENT DOCUMENTS

| | | |
|---|---|---|
| 0313836 A3 | 5/1989 | European Pat. Off. . |
| 0397173 A1 | 11/1990 | European Pat. Off. . |
| 0419277 A1 | 3/1991 | European Pat. Off. . |
| 0515201 A1 | 11/1992 | European Pat. Off. . |
| 8901797 | 3/1989 | WIPO . |
| 9005486 | 5/1990 | WIPO . |
| 92/14508 | 9/1992 | WIPO . |
| 93/04722 | 3/1993 | WIPO . |

OTHER PUBLICATIONS

United States Patent Application Serial No. 08/576,242, filed Dec. 21, 1995, naming Michael Schwager as the inventor, and commonly owned by the assignee of the above–captioned application.

United States Patent Application Serial No. 08/581,416, filed Dec. 29, 1995, naming Michael Schwager as the inventor, and commonly owned by the assignee of the above–captioned application.

*Primary Examiner*—Max Hindenburg
*Assistant Examiner*—Pamela L. Wingood
*Attorney, Agent, or Firm*—Philip C. Strassburger

[57] ABSTRACT

The pressure measuring guide wire comprises an elongated flexible shaft with a lumen extending therethrough. The lumen is surrounded by a wall forming the shaft and the distal portion of which is provided with slots for pressure medium entry. The distal portion has a thickness, greater than the thickness of the proximal area of the shaft. A coil surrounds the proximal area of the shaft to compensate the difference in kinking resistance between the proximal and distal areas of the shaft.

24 Claims, 3 Drawing Sheets

PRESSURE MEASURING GUIDE WIRE

BACKGROUND OF THE INVENTION

This invention relates to a pressure measuring guide wire comprising an elongated flexible shaft with a proximal portion, a distal portion, a lumen extending through the shaft, wall means surrounding said lumen, and aperture means for entry of a pressure medium into the lumen.

Intracoronary pressure recordings give valuable information to the cardiologist to assess both coronary and myocardial flow reserve and collateral blood flow.

The problem of pressure measuring guide wires is to provide an uninterrupted lumen throughout the shaft which has to be highly flexible to conform with the tortuous pathways of the blood vessels; simultaneously, the shaft must have a reasonably high stiffness to assure pushability and torque transmission thereto; and furthermore, the shaft must have a very good kink resistance to avoid the risk of constrictions resulting in modification of the advance of pressure waves through the lumen.

Current pressure measuring guide wires are made of a plastic tube and a stiffening wire. This is, however, very costly and leads to constrictions in the lumen which obstruct the advance of pressure waves in the lumen.

Another approach is shown in the document EP-A1-0419277 which describes a guide wire for use in measuring a characteristic of liquid flow in a vessel comprising a flexible elongate element in the form of a tube with a core wire provided therein the distal extremity of which is tapered and extends beyond the distal end of the tube. The tapered extremity of the core wire extends into a coil spring which is soldered to the tube. The coil spring is formed of two parts which are screwed together and the spring is bonded to the core wire by solder at the region where the two portions of the coil spring are screwed together. A safety wire extends from the joint of the two coils to the distal extremity of the coil spring where it is secured to a transducer carried by the distal end of the coil spring. Front and rear contacts are provided on the transducer and are connected to a two conductor wire which extends rearwardly and interiorly of the coil spring and further extends into the tube between the core wire and the interior of the tube to get out of the tube for connection to a male connector. According to a variant, an insulating sleeve may form a tight fit with the exterior surface of the core wire and it may also fit within the tube to insulate the core from the tube so that the core and the tube and core may serve as separate and independent electrical conductors.

It is an object of this invention to improve over the cited art by means of a pressure measuring guide wire which is easy and inexpensive to manufacture, which is highly versatile while having excellent qualities of pushability and resistance to kinking, and which allows a smooth advance of pressure waves through the lumen.

SUMMARY OF THE INVENTION

Towards fulfilling of these and other objects, the invention provides for a pressure measuring guide wire comprising an elongated flexible shaft with a proximal area, a distal area, a lumen extending through the shaft, wall means surrounding said lumen, and aperture means for entry of a pressure medium into the lumen, wherein said wall means have a first portion of length having a first resistance to kinking, a second portion of length having a second resistance to kinking, said second resistance to kinking being smaller than said first resistance to kinking, and wherein coil means are supporting said second portion of length. Accordingly, it becomes possible to modulate the resistance to kinking as a function of the structural organization for the pressure medium entry into the lumen. The wall thickness may be selected at will, whereby the shaft can be made flexible and stiff enough to be pushed. The resistance to kinking can be practically constant and the risk of constrictions due to kinking is eliminated. A stiffening wire is no more needed, and there is a better frequency behaviour for the fluid medium.

The first portion of length or the second portion of length may be in the distal area of the shaft, making it possible to select at will the configuration of the supporting coil means.

Where the first portion of length has a first thickness and the second portion of length a second thickness smaller than the first one, with the first portion of length having a plurality of slots formed therein for entry of the pressure medium, the mere choice of thickness allows mastering the difference in resistance to kinking due to the presence of the slots.

Within this frame, the first portion of length may have a first outer diameter and the second portion of length may have a second outer diameter smaller than the first outer diameter, whereby the coil means may surround the second portion of length. In this configuration, the coil means and diameters may be easily chosen to have the coil means in flush alignment with the first outer diameter, for having an overall outer diameter constant and reduced friction upon travelling through the blood vessels. And to assure simple positioning of the coil means on the second portion of length, this second portion of length may be preceded proximally by a third portion of length having a third outer diameter larger than said second outer diameter, with the coil means surrounding the second portion of length between said first and third outer diameters. In that configuration the coil means may also be in flush alignment with the first outer diameter for the same reason of diameter constancy and friction reduction.

Still within this frame, the first portion of length may have a first inner diameter and the second portion of length may have a second inner diameter larger than the first inner diameter, whereby the coil means may be located within the second portion of length. In this configuration, the coil means and diameters may also be easily chosen to have the coil means in flush alignment with the first inner diameter for having an overall outer shaft surface which is homogeneous while the inner diameter of the shaft remains constant.

In any of the arrangements with the first portion of length in the distal area of the shaft and with slots formed in the first portion of length, some of the slots may be proximal of the first portion of length with some other slots being distal of the first portion of length, thereby avoiding too many holes on the same diameter in order to minimize the risk of kinking resistance reduction in that area.

Where the second portion of length has a plurality of elongated slots formed therein for entry of the pressure medium and the coil means are located inside the shaft and extend at least under the slots, a very small thickness of the wall may be achieved all along the shaft, including the weakened area of slot location which is supported by the coil means which avoids the risk of kinking in that delicate area. And as the slots are fully supported by the coil means, they can be located at the same level along the second portion of length. To facilitate entry of the pressure medium, the coil means may have adjacent windings which are spaced apart from one another extending at least under the slots.

In order to stiffen the coil means without interfering with the shaft, core means may extend through the coil means. Where such core means have a proximal portion for longitudinal abutment against a proximal end of the coil means and a distal portion for longitudinal abutment with a distal end of the coil means, a stress free assembly is achieved which stiffens the turns of the coil means and which leaves the shaft lumen free of any obstruction proximally of the coil means. The core means may also have their proximal portion integral with a wire which extends proximally along and out of the lumen of the shaft. In that case, the supporting coil may be placed under the slots only for insertion of the guide wire to assure the required resistance to kinking. During insertion, the wire extending the core also has some stiffening effect for the shaft and improves its pushability. When the guide wire is properly located, the wire and supporting coil are removed from the guide wire to have the shaft lumen fully free of obstruction for pressure measurements.

In sum, the present invention relates to a pressure measuring guide wire having an elongated flexible shaft with a proximal area, distal area, a lumen extending through the shaft, wall means surrounding the lumen, and aperture means for entry of a pressure medium into the lumen. The wall means may have a first portion of length having a first resistance to kinking, and a second portion of length having a second resistance to kinking, the second resistance to kinking being smaller than the first resistance to kinking, and coil means supporting the second portion of length. The first portion of length may be in the distal area of the shaft. The second portion of length may be in the distal area of the shaft. The first portion of length may have a first thickness and the second portion of length may have a second thickness smaller than the first thickness, and the first portion of length may have a plurality of slots formed therein. The first portion of length may have a first outer diameter and the second portion of length may have a second outer diameter smaller than the first outer diameter, and the coil means may surround the second portion of length. The second portion of length may be preceded proximally by a third portion of length having a third outer diameter larger than the second outer diameter, and the coil means may surround the second portion of length between the first and third outer diameters. The coil means may be in flush alignment with the first outer diameter. The first portion of length may have a first inner diameter and the second portion of length may have a second inner diameter larger than the first inner diameter, and the coil means may be located within the second portion of length. The coil means may be in flush alignment with the first inner diameter. Some of the slots may be proximal of the first portion of length and some other slots may be distal of the first portion of length. The second portion of length may have a plurality of elongated slots formed therein, and the coil means may be located inside the shaft and extend at least under the slots. The elongated slots may be located at the same level along the second portion of length. The coil means may have adjacent windings which are spaced apart from one another, and extending at least under the slots. The pressure measuring guide wire may further have core means extending through the coil means, which may have a proximal portion for longitudinal abutment against a proximal end of the coil means, and a distal portion for longitudinal abutment with a distal end of the coil means. The proximal portion of the core means may be integral with a wire which extends proximally along and out of the lumen of the shaft. The shaft may be made of an elastic nickel titanium alloy, and the coil means may be made of high density metal such as tungsten. The distal area of the shaft may terminate in helical coil means defining a flexible assembly having a distal portion terminating into a tip. The helical coil means may be made of high density metal.

DESCRIPTION OF THE DRAWINGS

These and other objects, features and advantages of the invention will become readily apparent from the following detailed description with reference to the accompanying drawings which show, diagrammatically and by way of example only, three embodiments of the invention.

DESCRIPTION OF PREFERRED EMBODIMENTS

Figure 1:
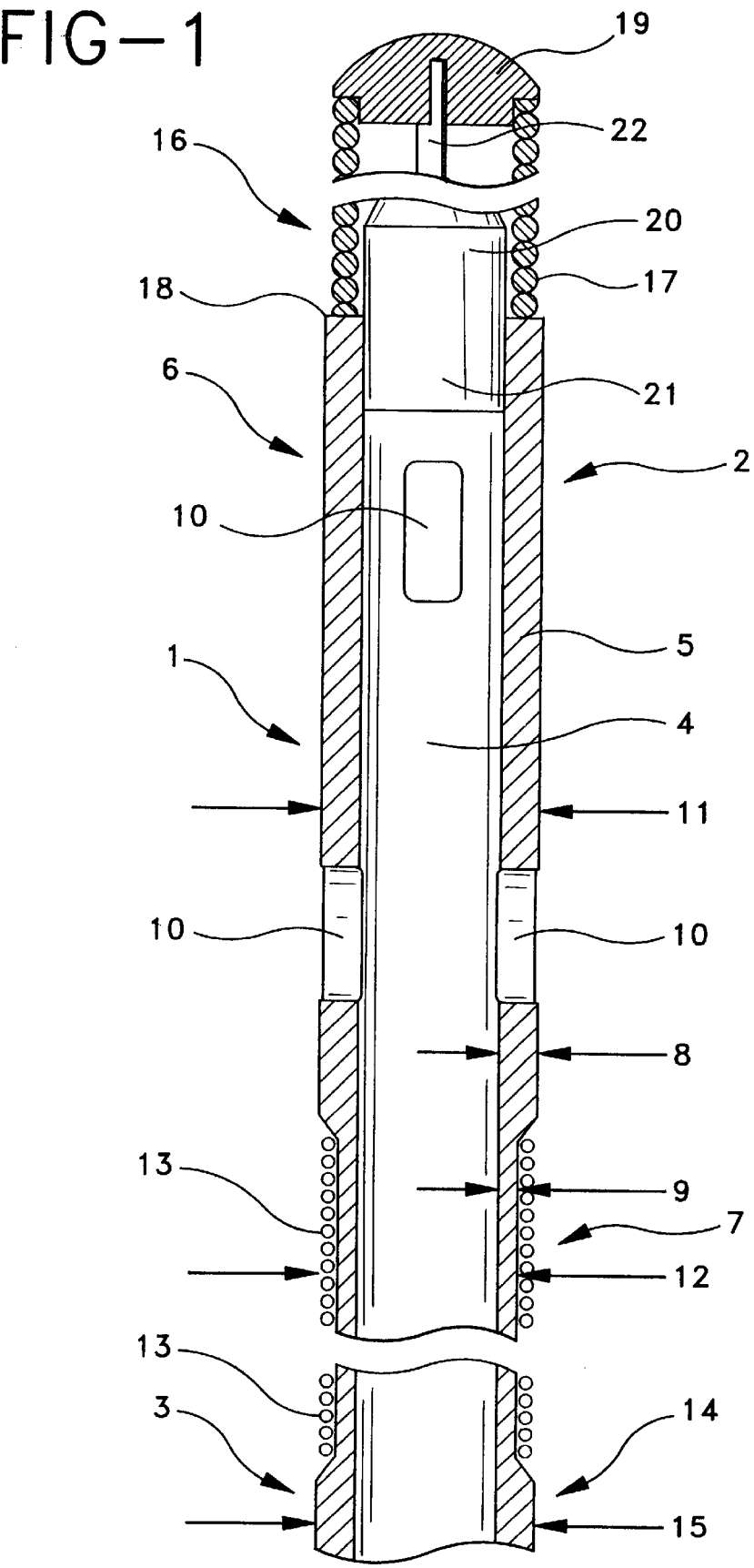
FIG. 1 is a cross sectional view of the first embodiment.

The guidewire shown in FIG. 1 comprises an elongated flexible shaft 1 having a distal area 2 and a proximal area 3. A lumen 4 extends through the shaft 1, and the proximal area 3 of the shaft is intended to be connected to a pressure measuring and monitoring equipment (not shown) common in the art.

Preferably, the shaft 1 is made of an elastic nickel titanium alloy such as for instance Nitinol™ or Tinel Alloy™. Other materials are also possible, for instance plastic materials.

The lumen 4 is surrounded by a wall 5 forming the shaft 1 and having a first portion of length 6 and a second portion of length 7. The first portion of length 6 is located in the distal area 2 of the shaft 1 and it has a first thickness 8; the second portion of length 7 is located in the proximal area 3 of shaft 1 and it has a second thickness 9, smaller than the first thickness 8, thereby achieving a resistance to kinking which is smaller than that of the first portion of length 6. The difference in thickness results from the fact that the first portion of length 6 has an outer diameter 11 longer than the diameter 12 of the second portion of length 7.

The first portion of length 6 has a plurality of slots 10 formed therein for entry of the pressure medium; some of these slots 10 are proximal of the first portion of length 6 and some other of these slots are distal of the first portion of length 6.

A coil 13, preferably of a high density metal such as for instance tungsten, is mounted on the second portion of length 7 for supporting purposes. This high density metal coil also provides a radiopaque reference for the first portion of length 6. This coil 13 is in flush alignment with the outer diameter 11 of the first portion of length 6.

The second portion of length 7 is preceded proximally by a third portion of length 14 of wall 5 having an outer diameter 15 greater than the second diameter 12, in the example shown, equal to the first outer diameter 11. The coil 13 is thus comprised between the first diameter 11 and the third diameter 15.

The distal area 2 of shaft 1 terminates in a flexible assembly 16 comprising a coil 17, preferably made of a high density metal such as tungsten, which also provides a radiopaque reference for the first portion of length 6 which is thus easily locatable between the two radiopaque references provided for by coils 13 and 17. The coil 17 abuts proximally on the distal end 18 of shaft 1 and its distal extremity terminates into a tip 19. A cylindrical core 20, for example of stainless steel, has its proximal portion 21 affixed, for instance welded, into the distal end 18 of shaft 1; core 19 tapers into a flattened straight and narrow distal portion 22 which terminates by welding into the tip 19.

Figure 2:
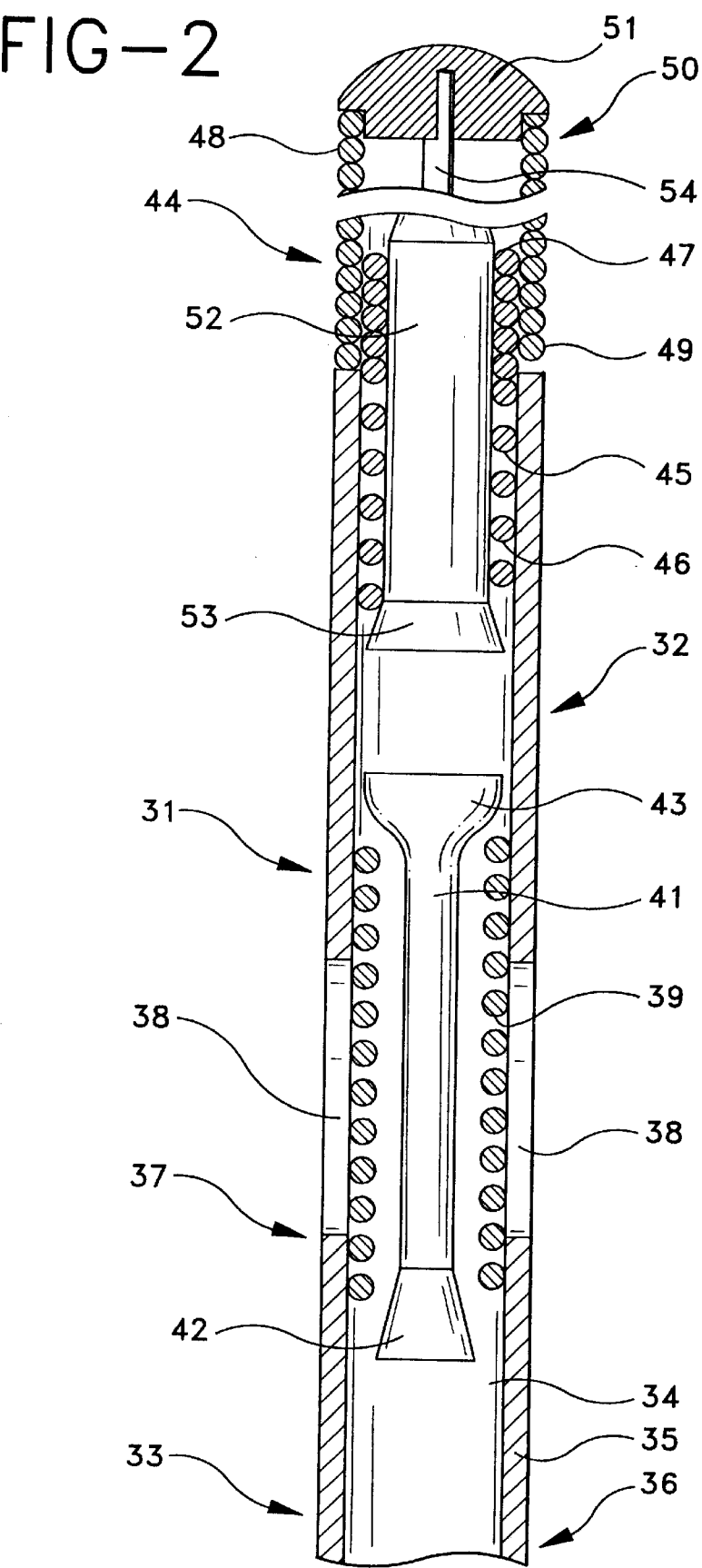
FIG. 2 is a cross sectional view of the second embodiment.

The guide wire shown in FIG. 2 also comprises an elongated flexible shaft 31 having a distal area 32 and a proximal area 33. A lumen 34 extends through the shaft 31, and as for the embodiment of FIG. 1 the proximal area 33 of the shaft 31 is intended to be connected to a pressure and monitoring equipment (not shown).

Preferably, the shaft 31 is also made of an elastic nickel titanium alloy such as Nitinol™ or Tinel Alloy™, but other materials such as plastic materials are also possible.

The lumen 34 is surrounded by a wall 35 forming the shaft 31 and having a first portion of length 36 and a second portion of length 37. The first portion of length 36 is located in the proximal area 33 of shaft 31; the second portion of length 37 is located in the distal area 32 of shaft 31 and it has a plurality of elongated slots 38 formed therein for pressure medium entry, thereby achieving a resistance to kinking which is smaller than that of the first portion of length 36 which is devoid of slots. The slots 38 may be located at the same level along the second portion of length 37, as shown.

A coil 39, preferably of a high density metal such as for example tungsten, is located inside the shaft 31 under the slots 38 for supporting the wall and slot structure and for providing a radiopaque reference for the second portion of length 37. This coil 39 extends somewhat beyond the slots 38 and, as shown, it may have adjacent windings which are spaced apart from one another to facilitate entry of the pressure medium within the lumen 34.

A core member 41, preferably in stainless steel, is located within the coil 39. This core member 41 has a proximal portion 42 in the form of a truncated cone for longitudinal engagement with the proximal end of the coil 39, and a distal portion 43 which is flattened so that the resulting enlargement abuts longitudinally against the distal end of the coil 39.

The distal area 32 of shaft 31 terminates in a flexible assembly 44, as described in European Patent Application No. 95103006.3 filed Mar. 2, 1995, comprising a first coil 45 having a proximal portion 46 and a distal portion 47, and a second coil 48 having a proximal portion 49 and a distal portion 50 ending in a weld tip 51. The proximal portion 46 of first coil 45 comprises adjacent windings which are spaced apart and this proximal portion 46 is threadedly force fitted into the tubular distal area 32 of shaft 31. An adhesive may be injected between the windings of proximal portion 46 of coil 45. This first coil is made of a high density metal, preferably tungsten, to provide a radiopaque reference for the flexible assembly 44. The second coil 48, also made of a high density metal such as tungsten, has its proximal portion 49 threadingly surrounding the distal portion of first coil 45 and abutting against the distal end of shaft 31. A cylindrical core 52, preferably of stainless steel, extends through the coil 45 and has a proximal portion 53 flattened so that the resulting enlargement abuts longitudinally against the proximal end 46 of coil 45. The core 52 tapers into a flattened straight and narrow portion 54 which terminates by welding into the tip 51.

Figure 3:
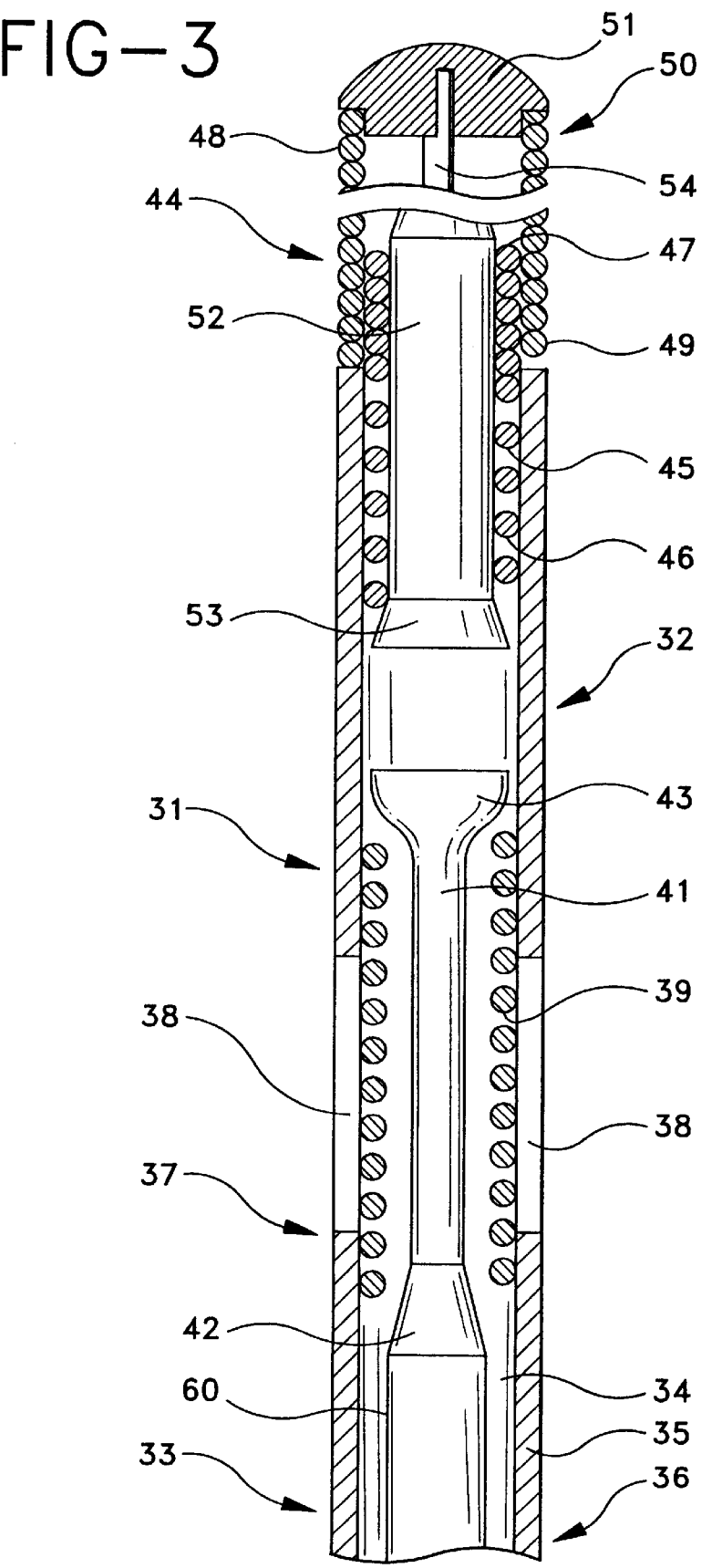
FIG. 3 is a cross sectional view of the third embodiment.

The guide wire shown in FIG. 3 comprises the same integers and corresponding reference numerals as the guide wire of FIG. 2. Additionally, core 41 has its truncated cone proximal portion 42 integral with the distal end of a wire 60 which extends along lumen 34 up to the proximal end of shaft 31 where it can be grasped for taking the assembly of core 41 and coil 39 out of the shaft 31. Accordingly, the coil 39 may be placed and maintained under the slots 38 only for insertion of the guide wire and withdrawn from the guide wire for pressure measuring.

Variants are available without departing from the scope of the invention.

For instance, the flexible assembly 16 of the first embodiment of FIG. 1 may be replaced by the flexible assembly 44 of the embodiment of FIG. 2 and vice versa.

The second portion of length 7 of the embodiment of FIG. 1 may have an inner diameter which is larger than the inner diameter of the first portion of length 6, whereby the coil 13 may be located inside the second portion of length 7, preferably in flush alignment with the inner diameter of the first portion of length.

I claim:

1. A pressure measuring guide wire comprising an elongated flexible shaft with a proximal area, distal area, a lumen extending through the shaft, wall means surrounding said lumen, and aperture means for entry of a pressure medium into the lumen, wherein said wall means have a first portion of length having a first resistance to kinking, a second portion of length having a second resistance to kinking, said second resistance to kinking being smaller than said first resistance to kinking, and wherein coil means are supporting said second portion of length.

2. A pressure measuring guide wire according to claim 1, wherein said first portion of length is in the distal area of the shaft.

3. A pressure measuring guide wire according to claim 1, wherein said second portion of length is in the distal area of the shaft.

4. A pressure measuring guide wire according to claim 2, wherein said first portion of length has a first thickness and said second portion of length has a second thickness smaller than said first thickness, and wherein said first portion of length has a plurality of slots formed therein.

5. A pressure measuring guide wire according to claim 4, wherein said first portion of length has a first outer diameter and said second portion of length has a second outer diameter smaller than said first outer diameter, and wherein said coil means surrounds said second portion of length.

6. A pressure measuring guide wire according to claim 5, wherein said second portion of length is preceded proximally by a third portion of length having a third outer diameter larger than said second outer diameter, and wherein the coil means surrounds the second portion of length between said first and third outer diameters.

7. A pressure measuring guide wire according to claim 5, wherein the coil means is in flush alignment with said first outer diameter.

8. A pressure measuring guide wire according to claim 4, wherein said first portion of length has a first inner diameter and said second portion of length has a second inner diameter larger than said first inner diameter, and wherein said coil means is located within said second portion of length.

9. A pressure measuring guide wire according to claim 8, wherein the coil means is in flush alignment with said first inner diameter.

10. A pressure measuring guide wire according to claim 4, wherein some of said slots are proximal of said first portion of length and some other slots are distal of the first portion of length.

11. A pressure measuring guide wire according to claim 3, wherein said second portion of length has a plurality of elongated slots formed therein, and wherein said coil means is located inside the shaft and extend at least under said slots.

12. A pressure measuring guide wire according to claim 11, wherein said elongated slots are located at the same level along said second portion of length.

13. A pressure measuring guide wire according to claim 11, wherein said coil means has adjacent windings which are spaced apart from one another, said spaced apart windings extending at least under the slots.

14. A pressure measuring guide wire according to claim 11, further comprising core means extending through the coil means.

15. A pressure measuring guide wire according to claim 14, wherein said core means has a proximal portion for longitudinal abutment against a proximal end of said coil means, and a distal portion for longitudinal abutment with a distal end of said coil means.

16. A pressure measuring guide wire according to claim 15, wherein the proximal portion of the core means is integral with a wire which extends proximally along and out of the lumen of the shaft.

17. A pressure measuring guide wire according to claim 1, wherein the shaft is made of an elastic nickel titanium alloy.

18. A pressure measuring guide wire according to claim 1, wherein said coil means is made of high density metal.

19. A pressure measuring guide wire according to claim 18, wherein the coil means is made of tungsten.

20. A pressure measuring guide wire according to claim 1, wherein the distal area of the shaft terminates in helical coil means defining a flexible assembly having a distal portion terminating into a tip.

21. A pressure measuring guide wire according to claim 20, wherein said helical coil means is made of high density metal.

22. A guidewire for use in pressure measurement, the guidewire comprising:
   (a) an elongate flexible assembly having an outer surface therealong and a lumen extending at least partially therethrough, the assembly having:
      (i) a first coil against the outer surface for supporting a first length of the assembly;
      (ii) a second coil supporting a second length of the assembly, the second coil against the outer surface and spaced proximally from the first coil in a non-overlapping configuration; and
      (iii) openings in the outer surface to allow the passage of pressurized fluid into the lumen.

23. A guidewire for use in pressure measurement, the guidewire comprising:
   (a) an elongate flexible assembly having an outer surface and a lumen extending at least partially therethrough, the assembly having:
      (i) a first coil against the outer surface for supporting a first length of the assembly;
      (ii) a second coil against the outer surface for supporting a second length of the assembly, the second coil spaced proximally from the first coil in a non-overlapping configuration; and
      (iii) openings in the outer surface disposed between the first and second coils to allow the passage of pressurized fluid into the lumen.

24. A guidewire for use in pressure measurement, the guidewire comprising:
   (a) an elongate flexible assembly having an outer surface and a lumen extending at least partially therethrough, the assembly having:
      (i) a first coil against the outer surface for supporting a first length of the assembly;
      (ii) a second coil against the outer surface for supporting a second length of the assembly, the second coil spaced proximally from the first coil in a non-overlapping configuration; and
      (iii) openings in the outer surface disposed about the second coil to allow the passage of pressurized fluid into the lumen.

* * * * *